(12) United States Patent
Fitelzon et al.

(10) Patent No.: US 9,375,287 B2
(45) Date of Patent: Jun. 28, 2016

(54) TARGET IDENTIFICATION TOOL FOR INTRA-BODY LOCALIZATION

(75) Inventors: Shai Fitelzon, Qadima (IL); Paige B. Hastings, Bloomington, MN (US); David J. McKinley, Chanhassen, MN (US)

(73) Assignee: Covidien LP, Mansfield, MA (US)

( * ) Notice: Subject to any disclaimer, the term of this patent is extended or adjusted under 35 U.S.C. 154(b) by 747 days.

(21) Appl. No.: 12/362,421

(22) Filed: Jan. 29, 2009

(65) Prior Publication Data

US 2009/0240140 A1 Sep. 24, 2009

Related U.S. Application Data

(60) Provisional application No. 61/062,914, filed on Jan. 29, 2008, provisional application No. 61/051,632, filed on May 8, 2008.

(51) Int. Cl.
*A61B 90/00* (2016.01)
*A61B 19/00* (2006.01)
*A61B 17/00* (2006.01)

(52) U.S. Cl.
CPC ....... *A61B 19/54* (2013.01); *A61B 2017/00889* (2013.01); *A61B 2017/00893* (2013.01); *A61B 2017/00942* (2013.01); *A61B 2090/392* (2016.02); *A61B 2090/3912* (2016.02); *A61B 2090/3945* (2016.02); *A61B 2090/3975* (2016.02); *A61B 2090/3991* (2016.02)

(58) Field of Classification Search
CPC .............. A61B 19/54; A61B 2017/00889; A61B 2017/00893; A61B 2017/00942; A61B 2019/5408; A61B 2019/5412; A61B 2019/542; A61B 2019/5445; A61B 2019/5466; A61B 2019/547; A61B 2019/5475; A61B 2019/5487; A61B 2019/5491
USPC .................................... 600/424, 426; 424/423
See application file for complete search history.

(56) References Cited

U.S. PATENT DOCUMENTS

| | | | | |
|---|---|---|---|---|
| 4,790,329 | A * | 12/1988 | Simon | 600/562 |
| 5,105,829 | A * | 4/1992 | Fabian et al. | 128/899 |
| 5,269,783 | A * | 12/1993 | Sander | 606/148 |
| 5,904,690 | A * | 5/1999 | Middleman et al. | 606/113 |
| 6,070,589 | A * | 6/2000 | Keith et al. | 128/898 |
| 6,402,777 | B1 | 6/2002 | Globerman et al. | |
| 6,450,978 | B1 * | 9/2002 | Brosseau et al. | 600/595 |
| 6,942,667 | B1 * | 9/2005 | Song | 606/916 |
| 7,144,363 | B2 * | 12/2006 | Pai et al. | 600/16 |
| 2003/0163160 | A1 * | 8/2003 | O'Malley et al. | 606/213 |

(Continued)

FOREIGN PATENT DOCUMENTS

| | | |
|---|---|---|
| EP | 1607048 A1 | 12/2005 |
| EP | 1 772 111 A2 | 4/2007 |
| WO | 02/41786 A2 | 5/2002 |

OTHER PUBLICATIONS

WIPO, International Search Report for International Application No. PCT/US2009/032490 mailed Mar. 13, 2009, 2 pages.

(Continued)

*Primary Examiner* — Katherine Fernandez

(57) ABSTRACT

A marker device that aids in the subsequent identification of a particular area is equipped with an anchoring device that prevents migration once placed in the tissue of that particular area. The device may include a chemical agent or drug that adds a therapeutic function to the marker device.

17 Claims, 4 Drawing Sheets

(56) References Cited

U.S. PATENT DOCUMENTS

| | | | |
|---|---|---|---|
| 2003/0163161 A1* | 8/2003 | Barron et al. | 606/232 |
| 2003/0167000 A1* | 9/2003 | Mullick et al. | 600/424 |
| 2004/0034357 A1* | 2/2004 | Beane et al. | 606/73 |
| 2004/0167391 A1* | 8/2004 | Solar et al. | 600/411 |
| 2005/0154293 A1* | 7/2005 | Gisselberg et al. | 600/420 |
| 2006/0058568 A1* | 3/2006 | Gross et al. | 600/3 |
| 2006/0155312 A1* | 7/2006 | Levine et al. | 606/153 |
| 2006/0173361 A1* | 8/2006 | Gorden | 600/478 |
| 2006/0276871 A1* | 12/2006 | Lamson et al. | 623/1.11 |
| 2007/0087026 A1* | 4/2007 | Field | 424/423 |
| 2007/0225593 A1* | 9/2007 | Porath et al. | 600/423 |
| 2007/0238979 A1* | 10/2007 | Huynh et al. | 600/420 |
| 2007/0238983 A1 | 10/2007 | Suthanthiran et al. | |
| 2007/0243225 A1* | 10/2007 | McKay | 424/423 |
| 2008/0121825 A1* | 5/2008 | Trovato | 250/506.1 |
| 2009/0048629 A1* | 2/2009 | Rabiner | 606/232 |
| 2009/0216115 A1* | 8/2009 | Seiler et al. | 600/426 |

OTHER PUBLICATIONS

Partial supplementary European Search Report corresponding to EP 09 70 5516.4, completed Feb. 9, 2015 and dated Feb. 16, 2015; (7 pp).

European Communication and Extended European Search Report dated Jun. 3, 2015, corresponding to European Patent Application No. 09705516.4; 13 pages.

European Communication, dated Jun. 19, 2015, corresponding to European Patent Application No. 09705516.4; 5 pages.

* cited by examiner

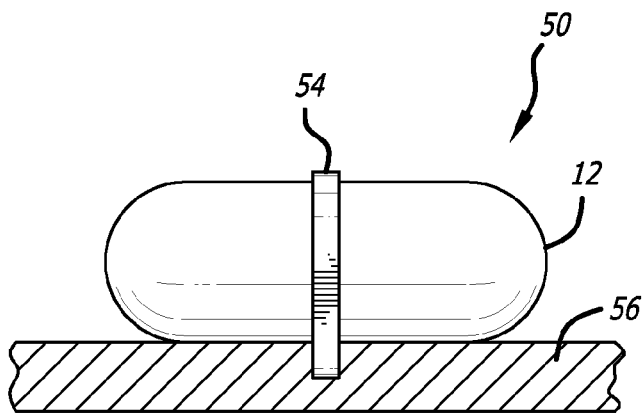
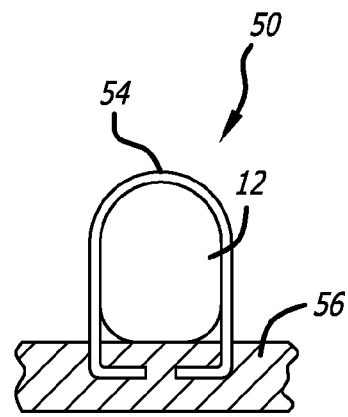
FIG. 9          FIG. 10
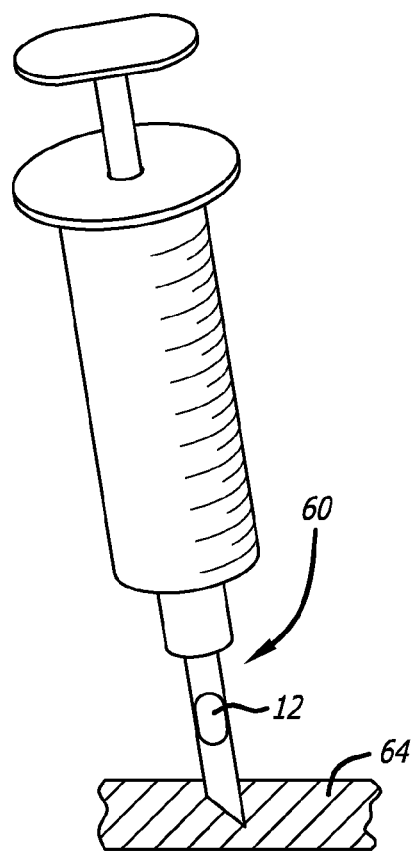
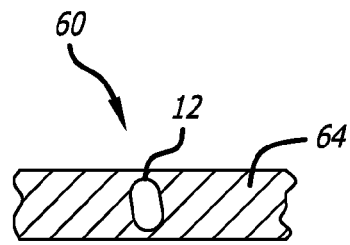
FIG. 11          FIG. 12

TARGET IDENTIFICATION TOOL FOR INTRA-BODY LOCALIZATION

PRIORITY CLAIM TO RELATED APPLICATIONS

This application is related to and claims priority from U.S. Provisional Application Ser. No. 61/062,914, filed Jan. 29, 2008, entitled Target Identification Tool For Intra-Body Localization, and U.S. Provisional Application Ser. No. 61/051,632, filed May 8, 2008, entitled Target Identification Tool For Intra-Body Localization. The entireties of each are incorporated by reference herein.

BACKGROUND OF THE INVENTION

In the case of a suspected lung mass in a high risk patient for lung cancer, it is the current standard of care to send the patient for radical removal of the mass. Certain portions of these surgeries are made by Video Assisted Thoracotomy Surgery (VATS), which is a minimally invasive surgery, and invasive Thoracic Surgery. Obtaining accurate diagnosis in the least invasive means possible as quickly as possible is essential. During VATS, it is often very hard to recognize the suspected small lung masses during the procedure. VATS success is limited by the ability to visualize and palpate the nodule if it is less than 10 mm in size and if it is more than 5 mm from a pleural surface. Historically, in 63% to 82% of cases there is an inability to visualize or palpate a detected nodule. (1. Burdine, et al. CHEST 2002; 122:1467, 2. Suzuki, et al. CHEST 1999; 115:563). Minimally invasive surgery is becoming more and more popular and holds similar challenges to those seen in VATS when used in the abdominal cavity, the urogenital system or other parts of the body.

A lung mass (solitary pulmonary nodules (SPN) or other) in the periphery of the lungs that is identified by X-ray machine or CT must also be physically identified by the surgeon for removal. However, visual identification of the mass may often be difficult due to tissue obstructions, such as, when the nodule is buried deep in the lung tissue.

Lack of visual identification creates problems. In some instances, surgeons discover lesions during surgery that were not earlier identified by a referring physician or radiologist. In this case, the surgeon needs to decide which of the lesions is suspected to be cancerous. Therefore, to avoid mistakes, the surgeon typically removes a larger portion of the tissue, ensuring the entire lesion is removed but also increasing tissue trauma, the possibility of complications, patient suffering, and so forth. In other cases, lack of visual identification results in the excision of healthy tissue rather than the targeted lesion.

In other body cavities similar challenges are encountered since visibility and the means to identify specific pre-planned lesions as were identified by medical imaging, is often limited.

Most current methods for identifying masses and other such lesions and tissues may best be characterized as "from the outside to the inside," and are often rather complex, invasive and risky. Such methods include, for example, manual identification (e.g., finger palpation through the rib cage), intrathorascopic ultrasound, transthoracic placement of an external wire, injecting solidifying liquids, dye injection, TC-99 injection, radiopaque markers such as barium or injectable coils, guidance by CT, intrathorascopic ultrasound, fluoroscopy-assisted thoracoscopic resection, etc.

There are current challenges with external beam radiation delivery due to the inability to see the tumor during treatment. Accurate alignment of sterotactic planning onto the patient, before the procedure, is required for accurate real-time tracking of the tumor. Additionally, tumor position in the lungs is changing as a result of the normal respiratory cycle, unpredictable baseline shifts and variable amplitude of respiratory rates. Consequently, an insufficient dose of radiation may be delivered due to its toxic effects on surrounding healthy lung tissue and may lead to failure to control tumor growth. Because of these challenges, fiducial markers are often used in soft tissue to guide focused-beam radiation treatment.

One of the major drawbacks to fiducial marker placement is delivery of the marker transthoracically. This approach can lead to pneumothorax or collapsed lungs because often the patients already have compromised lung function. In addition to the risk of pneumothorax there is also the complication of marker migration. Unlike the relatively static, homogeneous tissue of the prostate, the lung tissue moves significantly with the breathing cycle and is also porous and interlaced with airways. As a result, an implanted seed is prone to migrate, typically out of the channel formed during placement, and fall down an airway. Once in the airway, the seed will either settle in a distal portion of the lungs, or be coughed out.

Another potential application for marker or catheter placement within the lungs may be for the delivery of therapies such as brachytherapy, cryotherapy, or drug delivery through a deposited drug depot.

If an inert or active marker seed or temporary catheter migrates, the target is lost. If the therapy vehicle is expectorated, the treatment ends prematurely. Even worse, if the delivery vehicle migrates away from the target, therapy is administered to healthy tissue instead of a tumor, thereby damaging the healthy tissue and sparing the tumor.

There is a need for an improved identification device or marking device and method of introducing this device into the body. More specifically, there is a need for an identification device or marking device that: 1) can be placed within the location of interest or adjacent to it and permits identification of masses or other location of interest, through the surrounding tissues, 2) is minimally invasive, and 3) has a minimal damaging effect on the tissue to avoid complications.

There may also be a need for a method of extracting this device from the body in a minimally invasive manner.

There is also a need for anchoring an identification or therapeutic device or marking device within the body.

There is also a need for a method of communication or bringing between two tools, one from "inside out" and the other one from "outside in". The first is the so called identification device or marking device and the second is the complementary counterpart, which is an assembly of detector device and interventional device, capable to identify the signal emitted by the identification device or marking device, thus, the precision in localization is achieved and the task can be performed with great confidence.

There is also a need for a marker or therapeutic seed that includes an anchoring mechanism that prevents the seed from migrating once positioned.

OBJECTS AND SUMMARY OF THE INVENTION

In view of the foregoing, one aspect of the present invention is to provide an identification or marking device and method that overcomes the limitations of the prior art.

Another aspect of the present invention is to provide an identification or therapeutic device that may be placed permanently or semi-permanently (removable only with excision of the surrounding tissue) or removably (without significant trauma to the surrounding tissue).

Another aspect of the present invention is to provide an identification or therapeutic device that may be pre-, intra- or post operatively activated and implanted in the location of interest or adjacent to the location of interest within the body (for example, at or near a mass and surrounding tissues desired for extraction).

Another aspect of the present invention is to provide a body portion of the identification device that will be sufficiently illuminating to be seen through adjacent tissues and/or sufficient to indicate the exact location of interest by visualization of the light via the naked eye and/or through any kind of endoscope and/or sufficient to indicate the exact location of interest by sound, ultrasound, radioactive material electromagnetic emitting device or other form of energy.

Another aspect of the present invention is to provide a complementing counterpart, which is a permanent assembly or add-on detector device, coupled to an interventional device (e.g. light endoscope, Geiger meter), and capable of identifying the signal emitted by the identification device or marking device and communicating its location to the user.

Yet another aspect of the invention provides various anchoring devices that prevent the markers or therapeutic seeds of the present invention from migrating once implanted.

BRIEF DESCRIPTION OF THE DRAWINGS

FIG. 9 is a side view of the device of the device of the present invention;

FIG. 10 is an end view of the embodiment of the device of FIG. 9;

FIG. 11 is a perspective view of an embodiment of the device of the present invention being injected into body tissue;

FIG. 12 is a side view of the embodiment of the device of FIG. 11 implanted in tissue;

DETAILED DESCRIPTION OF THE INVENTION

In general, the present invention includes an identification or therapeutic device comprising a body portion and an anchoring portion, which is introducible into an intra-body structure (e.g., a mass or lesion) and/or an anatomical space to mark a location of interest (e.g., a tissue layer and/or lumen of a body cavity). The identification device of the present invention may include a power source, either external to the body or internally at or near the body portion or some combination thereof. It is understood that any of the various anchoring portions described below may be used with any of the body portions. It is also understood that the body portions may give off energy, such as light energy (i.e. glow-in-the-dark materials, LEDs, incandescent devices, etc.), thermal energy, radiation, RF energy, acoustic energy, or cryoenergy.

Furthermore, the various embodiments of the body portions may be constructed of various application-specific materials. For example, the body portions may be loaded with chemicals or dyes that enhance localization. Non-limiting examples include: BaSO4, bismuth, copper, gold, and platinum. Also, the body portions could be loaded with drugs and/or chemotherapy agents for treatment and have features such as controlled elution and diffusion rates. Non-limiting examples of these agents include antineoplastics, antibiotics and others.

Figure 1:
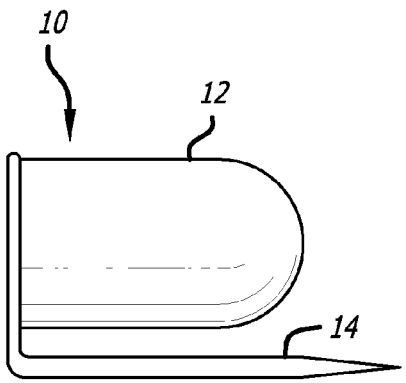
FIG. 1 is a side view of an embodiment of the device of present invention.
Figure 1A:
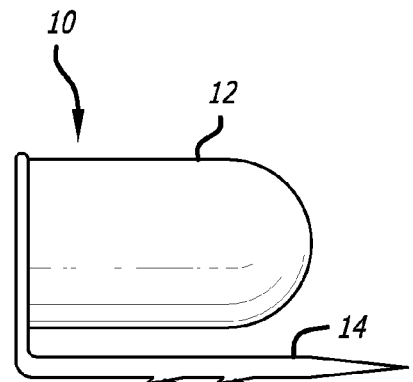
FIG. 1a is a side view of an embodiment of the device of the present invention.
Figure 2:
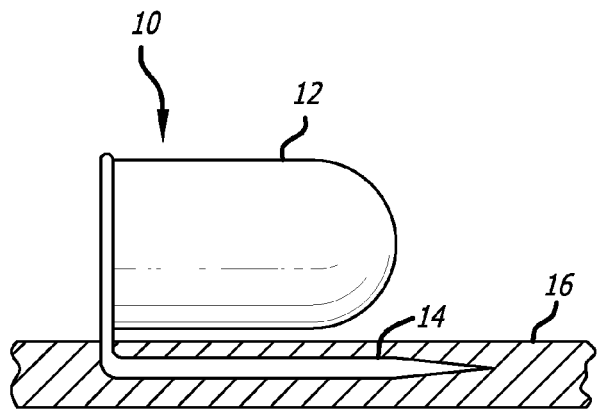
FIG. 2 is a side view of the embodiment of the device of FIG. 1 implanted into body tissue.

One embodiment of the present invention is shown in FIGS. 1, 1a, and 2 which illustrate an identification or therapeutic device 10, including a body portion 12 and anchoring portion 14. The body portion 12 may be any energy source or simply a marker or a focusing element for RF energy, as described above. If an energy source is used, it is understood that appropriate additional equipment will be used in order to receive and identify the energy being transmitted. The body portion 12 may also comprise a hollow body in the event that the device 10 is implanted in an airway.

The anchoring portion 14 is shaped and oriented to render it introducible into or adjacent to an intra-body structure. The anchoring portion 14, may also include hooks or barbs 15, to improve the anchoring ability of the anchoring portion 14. Preferably, the barbs 15 are small enough to allow removal with minimal tissue damage. As shown in FIG. 2, the anchoring portion of the identification or therapeutic device 10 is inserted into an intra-body structure (e.g., a tissue layer) 16. The anchoring portion 14 leaves the body portion 12 oriented adjacent to the tissue layer 16, providing fixed, yet removable illumination or therapy. ("Illumination" is being used in a general sense to include acoustic energy, radioactive energy, electromagnetic energy or other form of energy and should not be construed as being limited to casting visible light on a subject.) In this illustration of the embodiment, the device 10 may be pulled out of the tissue layer and removed from the body or the tissue may be excised with the identification device 10 still affixed thereto.

Figure 3:
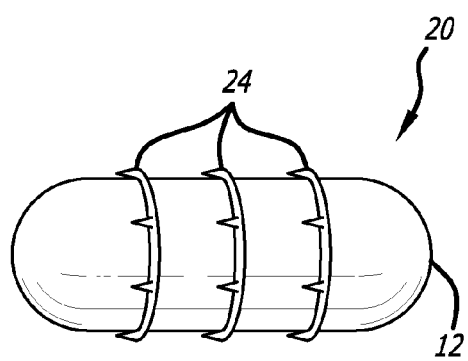
FIG. 3 is a perspective view of an embodiment of the device of the present invention.
Figure 4:
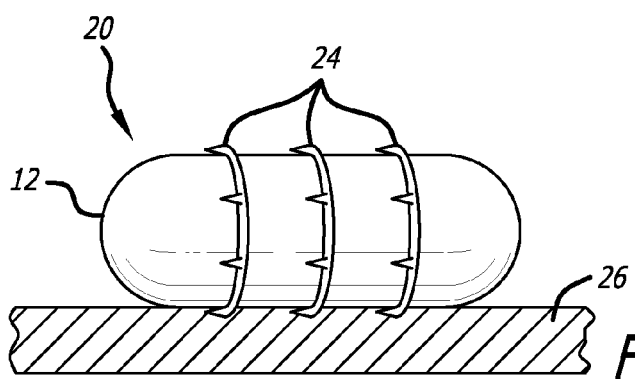
FIG. 4 is a perspective view of the embodiment of the device of FIG. 3 implanted into body tissue.

Another embodiment of the present invention is shown in FIG. 3, in which an identification or therapeutic device 20 includes a body portion 12 and at least one anchoring mechanism 24. The anchoring portion 24 is one or more barbed rings encircling the device 20. The barbs on the rings may be evenly spaced around the device 20, thereby providing ease of implantation as orientation-specific deployment is not necessary. Preferably, the barbs are strong enough to penetrate tissue yet flexible enough to lay flat in a deployment catheter. If the device 20 is intended to be non-permanent, the barbs should be short and flexible enough to allow removal without excessive tissue damage. FIG. 4 illustrates the device 20 inserted into an adjacent tissue layer 26 via the at least one anchoring mechanism 24.

Figure 5:
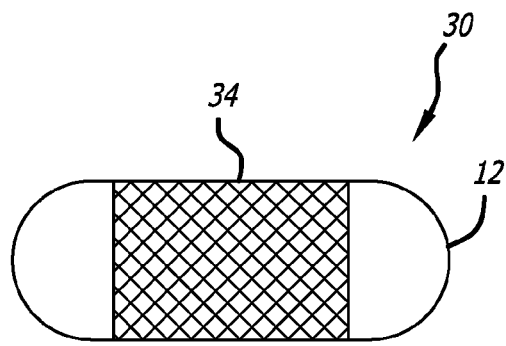
FIG. 5 is a perspective view of an embodiment of the device of the present invention.
Figure 6:
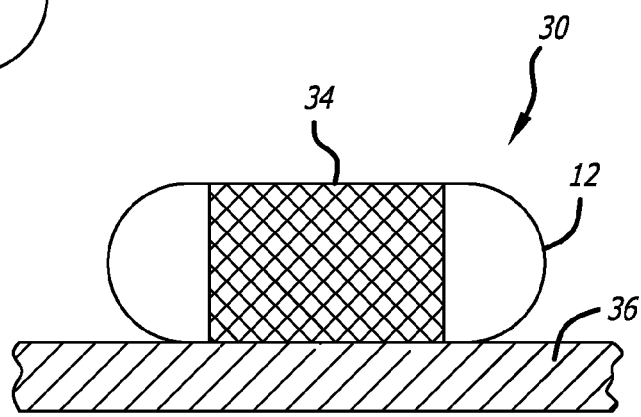
FIG. 6 is a perspective view of the embodiment of the device of FIG. 5 implanted into body tissue.

Yet another embodiment of the present invention is shown in FIG. 5, in which an identification or therapeutic device 30 includes a body portion 12 and an anchoring portion 34. The anchoring portion 34 includes, for example, a mesh and/or tissue adhesive affixed on at least a portion of the surface of the body portion 12. The mesh may be bioreactive. The anchoring portion 34 adheres to a tissue layer 36. The anchoring portion 34 is large enough to connect with the tissue layer 36, such that it will remain attached until some amount of applied force is used to remove the identification device 30 from the tissue layer 36. FIG. 6 illustrates the identification device 30 affixed to a tissue layer 36.

Figure 7:
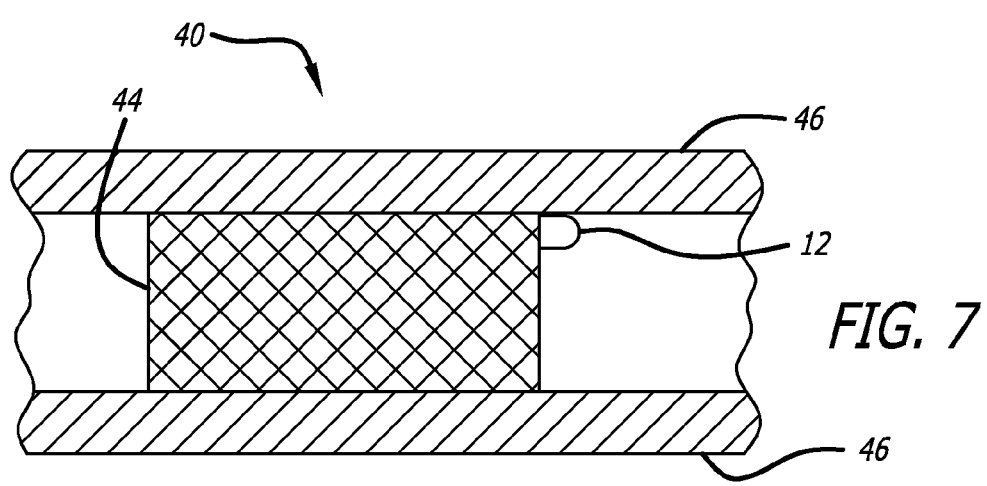
FIG. 7 is a perspective view of an embodiment of the device of the present invention.
Figure 8:
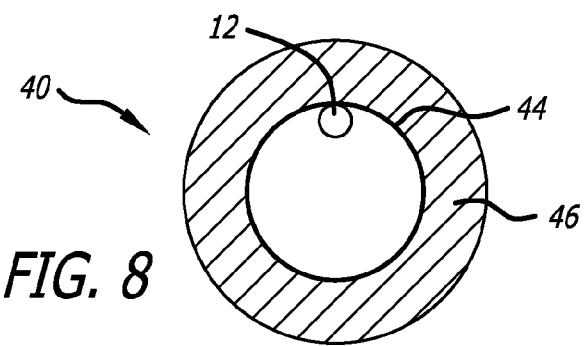
FIG. 8 is an end view of the embodiment of the device of FIG. 7 of the present invention.

Another embodiment of the present invention is shown in FIGS. 7 and 8, in which an identification or therapeutic device 40 includes a body portion 12 and an anchoring portion 44. In this embodiment, the anchoring portion 44 is disposed within a body lumen and may or may not penetrate the surrounding tissue layer 46. One example of the anchoring portion 44 contemplated for use in this embodiment of the invention would include a coil or stent 44 with a body portion 12 attached to an inside surface of the stent 44. The anchoring portion 44 expands, either via balloon or self-expanding design, to fit the surrounding tissue layer 46. The anchoring portion 44 is deliverable by any known or unknown methods. For example, the anchoring portion 44 may be collapsed to fit in or around a delivery catheter (not shown) and delivered and expanded in a desire location.

Another embodiment of the present invention is shown in FIGS. 9 and 10, in which an identification or therapeutic device 50 includes a body portion 12 and an anchoring portion 54. In this embodiment, the anchoring portion 52 is a staple that connects the device 50 to a tissue layer 56. Removal of the identification device 50 may occur via excision of all or part of the surrounding tissue layer 56.

The identification devices described above may be introduced and placed into the body by various delivery devices and methods. Such delivery devices and methods may include, alone or in combination, use of catheters, guiding catheters, guide wires, stents, balloons, needles, bronchoscopy procedures and tools and/or the superDimension localization system, as described in U.S. patent application Ser. No. 11/571,796 filed on Jan. 8, 2007, which is incorporated by reference herein in its entirety. In particular, such deliveries may be made into branches of the lungs, blood vessels and other points of interest (body cavities, lumens).

For example, one embodiment of a device 60 of the present invention that is injected into tissue is shown in FIGS. 11 and 12. The identification device 60 includes a body portion 12 that is injected into a tissue layer 64. The surrounding tissue layer 64 may effectively hold the identification device 60 in place. However, an additional anchoring portion may be added, such as any of the above described anchoring portions or merely a rough surface to prevent migration. FIG. 11 illustrates a needle 66 containing an identification or therapeutic device 60 prior to delivery into a tissue layer 64. FIG. 12 illustrates the placement of the identification device 60 within the tissue layer 64, post-injection.

Figure 13:
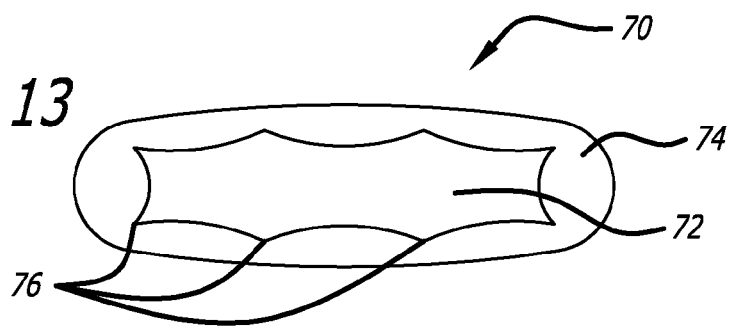
FIG. 13 is a side elevation of an embodiment of the device of the present invention; and, FIGS. 14 and 15 are side elevations of the device of FIG. 13 being implanted into tissue.
Figure 14:
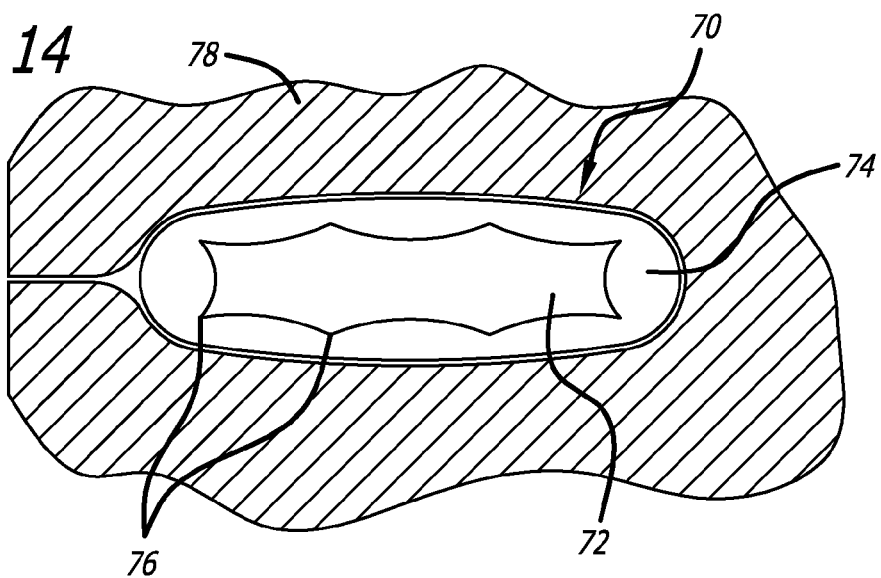
Figure 15:
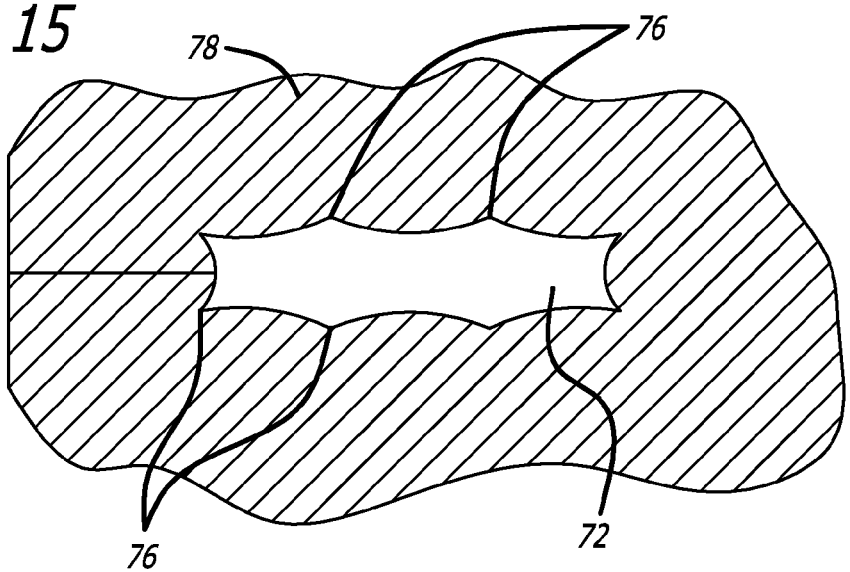

FIGS. 13-15 illustrate an embodiment of a device 70 of the present invention that is specifically designed to be injected into tissue. The device includes a capsule 74 surrounding the body portion 72 to allow the device 70 to be smoothly injected into tissue 78. Once in contact with the tissue, the capsule 74 quickly dissolves, allowing the tissue 78 to close in around the body portion 72. Preferably, the body portion 72 includes one or more anchoring features 76, such as ridges, spikes, rough surfaces, barbs, or other shapes or mechanisms that would prevent the device 70 from migrating.

The capsule 74 is smooth such that minimal tissue trauma occurs during insertion. The capsule may be constructed, for example, of a quickly dissolving material such as many water-soluble polymers.

Another embodiment of the present invention includes a device that is specifically designed to be injected into the target location for external localization. The entire device may be dissolvable or biodegradable thus eliminating the necessity for removal. The biodegradable material may be impregnated with a material such as metallic particles specifically selected to for image-guidance. The rate of degradation could be dependent on a known therapeutic dose to control or affect the targeted disease tissue. Examples of some biodegradable polymers include, but are not limited to: PEVA poly(ethyl-vinyl-acetate), PBMA poly(butyl-methylacrylate), PLGA poly(lactic-glycolic acid), PLA (Polylactide), PLGA/PLA combination, HA (hydroxyapetite), PLGA-PEG (polyethylene glycol), Tyrosine derivatives, Polyanhydrides, Polyorthoesters, PBMA, DLPLA—poly(dl-lactide), LPLA—poly(l-lactide), PGA—polyglycolide, PDO—poly (dioxanone), PGA-TMC—poly(glycolide-co-trimethylene carbonate), PGA-LPLA—poly(l-lactide-co-glycolide), PGA-DLPLA—poly(dl-lactide-co-glycolide), LPLA-DL-PLA—poly(l-lactide-co-dl-lactide), PDO-PGA-TMC—poly(glycolide-co-trimethylene carbonate-co-dioxanone). Examples of metallic or other image-guidance materials include but are not limited to: radiopaque dyes or contrast agents such as BaSO4 or Ominpaque, metallic particles such as copper or gold particles.

Although the invention has been described in terms of particular embodiments and applications, one of ordinary skill in the art, in light of this teaching, can generate additional embodiments and modifications without departing from the spirit of or exceeding the scope of the claimed invention.

For example, the above-described needle and syringe or plunger arrangement could be used to deliver an identification or therapeutic device internally, injecting said tool directly into a tissue layer from within the body cavity. Alternatively, a needle of sufficient construction both to penetrate the chest cavity (e.g., between the ribs of a patient) and accommodate the dimensions of an identification or therapeutic device such that can be injected from outside a patient's body into a desired location (e.g., directly into surrounding tissues near a body cavity; into a fibroid or tumor that is intended to be excised from the body; etc).

The identification device could be delivered via a bronchoscope having a catheter attached therethrough which is advanced through the lungs of a patient to a point of interest. The catheter will be equipped to push the identification device into a lumen of a body cavity near a tissue layer or into a tissue layer.

Accordingly, it is to be understood that the drawings and descriptions herein are proffered by way of example to facilitate comprehension of the invention and should not be construed to limit the scope thereof.

We claim:

1. A device, deliverable through a catheter in a proximal to distal direction, for marking a target location in a patient's body comprising:

a body portion locatable using a locating modality and configured to mark the target location, the body portion defining a longitudinal length and including a proximal end and a dosed distal end, the body portion configured to be inserted in tissue in the proximal to distal direction; and an anchoring portion having a proximal end and a sharpened distal end and defining a longitudinal length therebetween, the longitudinal length of the anchoring portion longitudinally extending at least partially along the longitudinal length of the body portion, the proximal end of the anchoring portion connected to the proximal end of the body portion and the sharpened distal end of the anchoring portion disposed in spaced relation to the body portion to define a longitudinally extending space between the anchoring portion and the body portion such that movement of the body portion in the proximal to distal direction is adapted to draw the tissue into the longitudinally extending space to prevent migration of the body portion within the tissue, wherein the sharpened distal end of the anchoring portion extends distally beyond the closed distal end of the body portion.

2. The device of claim 1, wherein the anchoring portion includes at least one hook.

3. The device of claim 1, further comprising a power source operably associated with the body portion and useable to create an indication of a location of the body portion.

4. The device of claim 1, wherein the body portion comprises an energy source.

5. The device of claim 4, wherein the energy source is configured to emit energy selected from the group consisting of light, heat, radiation, radiowaves, sound, and cryoenergy.

6. The device of claim 1, wherein the body portion includes a localization-enhancing chemical.

7. The device of claim 6, wherein the localization-enhancing chemical comprises a localization-enhancing dye.

8. The device of claim 6, wherein the localization-enhancing chemical is selected from the group consisting of BaSO4, bismuth, copper, gold, and platinum.

9. The device of claim 1, wherein the body portion includes a drug.

10. The device of claim 9, wherein the drug comprises a chemotherapy agent.

11. The device of claim 10, wherein the chemotherapy agent is selected from the group consisting of antineoplastics and antibiotics.

12. The device of claim 1, wherein the closed distal end of the body portion is curved and the proximal end of the body portion is planar.

13. The device of claim 1, wherein the anchoring portion includes at least one barb extending therefrom.

14. The device of claim 1, wherein the anchoring portion longitudinally extends the entire longitudinal length of the body portion.

15. A device, deliverable through a catheter in a proximal to distal direction, for marking a target location in a patient's body comprising:
 a hollow and smooth body portion locatable using a locating modality and configured to mark the target location, the body portion defining a longitudinal length and including a closed proximal end and a closed distal end, the body portion configured to be inserted in tissue in the proximal to distal direction; and
 an anchoring portion having a proximal end and a sharpened distal end and defining a longitudinal length therebetween, the longitudinal length of the anchoring portion longitudinally extending at least partially along the longitudinal length of the body portion, the proximal end of the anchoring portion connected to the closed proximal end of the body portion, the sharpened distal end of the anchoring portion extending perpendicularly from the proximal end of the anchoring portion and disposed in spaced relation to the body portion to define a longitudinally extending space between the anchoring portion and the body portion such that movement of the device in the proximal to distal direction is adapted to draw the tissue into the longitudinally extending space to prevent migration of the body portion within the tissue, wherein the sharpened distal end of the anchoring portion extends distally beyond the closed distal end of the body portion.

16. The device of claim 15, wherein the closed distal end of the body portion is curved and the closed proximal end of the body portion is planar.

17. The device of claim 15, wherein the anchoring portion longitudinally extends the entire longitudinal length of the body portion.

* * * * *